(12) United States Patent
Chi

(10) Patent No.: US 8,226,540 B1
(45) Date of Patent: Jul. 24, 2012

(54) ACUPUNCTURE NEEDLE WITH MAGNETIZED HANDLE

(76) Inventor: Tom Chi, South Fallsburg, NY (US)

( * ) Notice: Subject to any disclaimer, the term of this patent is extended or adjusted under 35 U.S.C. 154(b) by 663 days.

(21) Appl. No.: 12/359,304

(22) Filed: Jan. 24, 2009

(51) Int. Cl.
*A61B 17/52* (2006.01)
*A61B 17/34* (2006.01)
*A61H 39/08* (2006.01)

(52) U.S. Cl. ............................................. 600/9; 606/189
(58) Field of Classification Search ................ 600/9–15; 606/189
See application file for complete search history.

(56) References Cited

U.S. PATENT DOCUMENTS

| 6,231,584 | B1 * | 5/2001 | Gavronsky ................... 606/189 |
| 6,432,036 | B1 * | 8/2002 | Kim .................................. 600/9 |
| 2005/0021067 | A1 * | 1/2005 | Kim ............................. 606/189 |
| 2005/0080442 | A1 * | 4/2005 | Pessin .......................... 606/189 |
| 2009/0157112 | A1 * | 6/2009 | He ................................ 606/189 |

FOREIGN PATENT DOCUMENTS

| CN | 1060036 | * | 9/1990 |
| CN | 1081097 | * | 1/1994 |
| CN | 1223852 | * | 7/1999 |
| DE | 3302406 | A1 * | 7/1984 |

\* cited by examiner

*Primary Examiner* — Miranda Le
*Assistant Examiner* — Meredith Weare
(74) *Attorney, Agent, or Firm* — Michael I. Kroll

(57) ABSTRACT

An acupuncture needle having a low magnetized or non magnetized needle shaft or shank portion and a magnetic or magnetized handle portion to deliver both penetration and magnetic treatment to an acupuncture point.

11 Claims, 11 Drawing Sheets

ACUPUNCTURE NEEDLE WITH MAGNETIZED HANDLE

BACKGROUND OF THE INVENTION

1. Field of the Invention

The present invention relates generally to acupuncture and, more specifically, to an acupuncture needle having two distinct portions comprising a non or low magnetizable needle shaft portion that is seated and fixed into the aperture of a magnetic handle.

A main feature of the invention is the use of a magnetic or magnetizable handle made of neodymium iron boron (NdFeB) or other magnetic material. In this way the handle can be magnetized to supply a magnetic charge down the shaft and into the acupuncture point that is far superior to that which would occur if an ordinary acupuncture needle and shaft were to be magnetized. This allows for a stainless or similar needle shaft with the handle comprised of a material much more magnetizable than stainless steel and other materials including plastic handles that are nonmagnetic and naturally do not rust.

Another main feature of the invention is the ability to mix nylon or other injectable or moldable material with the magnetizable (NdFeB) allowing complete control over how much flux the magnet will produce.

Another feature of the invention is that the NdFeB may be melted for injection molding or may be a powder when mixed with plastic, glue, etc., for the molding process.

The needle shaft portion of the present invention is initially non-magnetized during manufacture and minimizes any particles the needle may pick up as the result of a magnetic field.

The handle of the needle may be constructed of either a natural magnet e.g. neodymium or any suitable magnetizable material.

The needle may be packaged and magnetized after sterilization and shipped ready for use or may be field magnetized.

The present invention further provides another method of manufacturing these magnetizable needles quite simply by gluing NdFeB (or similar) powder to a standard needle handle resulting in a highly magnetizable handle but a simplified manufacturing process.

The present invention additionally provides for the use of a magnetized sleeve which can be used to field magnetize the needle prior to or during treatment. Additionally the magnetized sleeve of the present invention has a slit from end to end to allow use while the needle is inserted into a patient so as to allow for lateral removal from the needle. The magnetized sleeve works by being passed over the needle in one direction. To remove it in the same direction would then demagnetize the needle. The slit in the side allows the device to be used and removed without reversing the magnetic effect.

When magnetized, the needle produces an electromagnetic field whereby the flux is sufficient enough to extend into the acupuncture point during typical acupuncture treatment of a patient, thereby increasing the electromagnetic activity at the point.

In production the handle may be composed of a homogeneous magnetic material, or a plastic compound imbued with material such as Neodymium Iron Boron that allows for magnetization. Additionally the magnetic shaft can be formed into different shapes as in the case of an ear needle.

2. Description of the Prior Art

There are other acupuncture devices designed for carrying a magnetic charge. Typical of these is U.S. Pat. No. 4,161,943 issued to Nogier on Jul. 24, 1979.

Another patent was issued to Kief on Apr. 21, 1981 as U.S. Pat. No. 4,262,672. Yet another U.S. Pat. No. 4,508,119 was issued to Tukamoto on Apr. 2, 1985 and still yet another was issued on Sep. 5, 2000 to Chung as U.S. Pat. No. 6,113,620.

Another patent was issued to Kim on Aug. 13, 2002 as U.S. Pat. No. 6,532,036. Yet another U.S. Pat. No. 6,488,668 was issued to Prindle on Dec. 3, 2002. Another was issued to Xie on Aug. 31, 2004 as U.S. patent No. Aug. 31, 2004 and still yet another was issued on Jan. 23, 2007 to Lin-Hendel as U.S. Pat. No. 7,167,752.

Another patent was issued to Wang on Apr. 8, 1992 as China Patent No. CN1060036. Yet another International Patent Publication No. WO98/02128 was published to Chung on Jan. 22, 1998. Another was issued to Moon et al. on Feb. 25, 2004 as Korea Patent No. KR20040016928.

U.S. Pat. No. 4,161,943

Inventor: Paul Nogier

Issued: Jul. 24, 1979

An apparatus for implanting magnetized or magnetizable needles, which apparatus comprises a tubular body, means to support a flat needle of small dimensions, made of a magnetizable metal, and means to drive the said needle into the tissues. A permanent magnet, taking the form of a substantially circular flat tablet is inserted in closed end of the body with one of its sides exposed outwardly of same. When the needle has been implanted, it may be magnetized or remagnetized as often as required by merely applying the exposed side of the tablet against the tail of the needle. In a modification the body of the apparatus is provided with a socket-like protecting cap and the tablet is inserted in the closed end of this cap, the needle supporting means being so arranged that the tip of the needle is situated close to the said closed end of the cap in order to be already magnetized by the tablet before the needle is implanted.

U.S. Pat. No. 4,262,672

Inventor: Horst Kief

Issued: Apr. 21, 1981

An acupuncture instrument for use in producing analgesia comprises a needle having a head and an electrical connection for applying a transformer arrangement including an electric coil constituting a secondary winding of the transformer arrangement and having two poles, one of the poles being insulated therefrom, the electric coil being arranged on the needle head and being capable of being surrounded by another coil constituting a primary winding of the transformer arrangement, and an annular electrode electrically connected to the other pole of the secondary winding and insulated with respect thereto and vertically movably arranged on the secondary winding.

U.S. Pat. No. 4,508,119

Inventor: Kenkichi Tukamoto

Issued: Apr. 2, 1985

A needle having at least one of magnetic field and electrostatic field improves effects of acupuncture in Oriental medical therapy. Further, a magnetized and/or electrostatically charged injection needle can be used for so-called "block therapy".

U.S. Pat. No. 6,113,620

Inventor: Joong Suck Chunk

Issued: Sep. 5, 2000

A magnetic needle for acupuncture is disclosed. The magnetic needle of this invention has a housing having an opening and a magnet seated in the opening of the housing. A wedge-shaped projection is held in the opening of the housing so as to project into the exterior of the bottom wall of the housing and come into contact with the magnet. The projection forms an intensive magnetic field around a meridian point having fine electric current or electromagnetic waves. The projection thus magnetically stimulates the meridian point while performing a magnetic massage effect on the meridian point. The magnetic needle accomplishes an acupuncturing effect for relieving pain and curing disease as expected in typical acupuncture.

U.S. Pat. No. 6,432,036

Inventor: Chi-Kyung Kim

Issued: Aug. 13, 2002

A device for magnetic focus radiating medical treatment is disclosed. The device has a support member holding both a magnet and a needle therein in a way such that the magnet comes into contact with the needle. The magnet is used for generating lines of magnetic force, while the needle is used for radiating the lines of magnetic force from the magnet onto a desired part of the human body. A hollow casing receives the support member therein with the tip of the needle being selectively projected from the lower end of the casing. This casing has an external thread at its lower end. An outside plug detachably covers the top end of the casing. A cap is movably tightened to the external thread of the casing. This cap also has a needle hole at a central portion of its wall so as to allow the needle to pass through the needle hole. In the above device, the exposed length of the needle outside the cap is adjustable as desired by appropriately tightening or loosening the internally threaded cap relative to the externally threaded casing.

U.S. Pat. No. 6,488,668

Inventor: Gordon Prindle

Issued: Dec. 3, 2002

A device for magnetic focus radiating medical treatment is disclosed. The device has a support member holding both a magnet and a needle therein in a way such that the magnet comes into contact with the needle. The magnet is used for generating lines of magnetic force, while the needle is used for radiating the lines of magnetic force from the magnet onto a desired part of the human body. A hollow casing receives the support member therein with the tip of the needle being selectively projected from the lower end of the casing. This casing has an external thread at its lower end. An outside plug detachably covers the top end of the casing. A cap is movably tightened to the external thread of the casing. This cap also has a needle hole at a central portion of its wall so as to allow the needle to pass through the needle hole. In the above device, the exposed length of the needle outside the cap is adjustable as desired by appropriately tightening or loosening the internally threaded cap relative to the externally threaded casing.

U.S. Pat. No. 6,783,504

Inventor: Robert Be Xie

Issued: Aug. 31, 2004

A method for effective weight loss without negative or harmful side effects as well as for the treatment of ailments in human patients. Treatment is achieved using a combination of acupuncture and magnets. The method includes the steps of placing several acupuncture needles into specified locations on the human body, removing the acupuncture needles, and placing several magnets onto the same locations that the needles previously occupied. Another important object of the present invention is to provide and effective method of coping with and managing diabetes.

U.S. Pat. No. 7,167,752

Inventor: Catherine Lin-Hendel

Issued: Jan. 23, 2007

An electronic acupressure aide and stimulating device implemented using a hand-held or palm-held electronic computing device or another computing device which may be a designated unit. The electronic acupressure aide and stimulating device allows a practitioner to apply a pulse sequence to a set of predetermined acu-points such as those related to acupressure, acupuncture, trigger points or Jin-Shin Jyutsu, to name a few. A displayed chart related to the acu-points identifies the health condition and the pulse sequence.

China Patent Number CN1060036

Inventor: Dianchen Wang

Issued: Apr. 8, 1992

The present invention relates to a kind of miniature strong magnetism therapeutic device which is composed of a dia 24 mm multiply 27 mm Nd—Fe—B permanent magnet, a dia 24 mm bottom, dia 3 mm top and 10 mm height conoid which is punched a 2 mm straight hole on centre, and aluminum alloy casing and housing. The magnetic field intensity at top surface of said invention is 6000 Gauss. When it is used for massage or needle press on affected part or acupuncture point, the magnetic beam with penetrating feeling is radiated on human body to improve the blood circulation of local muscle or joint and to variate the excitation and inhibition of central nervous system, thus producing the analgesic action. If it is used for curing muscular spasm, lumbocrural pain, arthritis and neuralgia, it has quick analgesic and antispasm curative effects and no by-effects.

International Patent Publication Number WO 98/02128

Inventor: Joong Suk Chung

Published: Jan. 22, 1998

A magnetic needle for acupuncture is disclosed. The magnetic needle of this invention has a housing having an opening and a magnet seated in the opening of the housing. A wedge-shaped projection is held in the opening of the housing so as to project into the exterior of the bottom wall of the housing and come into contact with the magnet. The projection forms an intensive magnetic field around a meridian point having fine electric current or electromagnetic waves. The projection thus magnetically stimulates the meridian point while performing a magnetic massage effect on the meridian point. The magnetic needle accomplishes an acupuncturing effect for relieving pain and curing disease as expected in typical acupuncture.

Korea Patent Number KR20040016928

Inventor: Choi Bok Moon et al

Published: Feb. 25, 2004

PURPOSE: Provided are an acupuncture needle using bamboo, charcoal and a magnet having beneficial effects on the human body, and a manufacturing method thereof, to suppress pain by pressing acupuncture spots and to enhance a user's health and vitality by stimulating blood circulation and generating far-infrared radiation. CONSTITUTION: The acupuncture needle (6) comprises: a bamboo cylinder (2); an energy radiating plate (1) and a circular magnet (3) provided at a bamboo node (4); and a charcoal rod (5) filling the bamboo cylinder (2). The acupuncture needle is prepared by putting a circular magnet and a charcoal rod into the bamboo cylinder and sealing with the energy radiating plate.

While these acupuncture techniques may be suitable for the purposes for which they were designed, they would not be as suitable for the purposes of the present invention, as hereinafter described.

SUMMARY OF THE PRESENT INVENTION

A primary object of the present invention is to provide an acupuncture needle having a magnetized or magnetizable handle portion to deliver both penetration and magnetic treatment to an acupuncture point.

Another object of the present invention is to provide an acupuncture needle having a handle portion that may be magnetized or re-magnetized by the passing through of a magnetic sleeve during application to the patient.

Yet another object of the present invention is to provide an acupuncture needle having a shaft portion that in inherently productive in producing and/or conducting the flux to produce a magnetic field.

Another object of the present invention is to provide an acupuncture needle having primarily a strong magnetic handle that has a determinate strength in accordance to the amount of mixed plastic and magnetic material.

Yet another object of the present invention is to provide an acupuncture needle having a needle shaft of reasonably low magnetic nature to create less of a concern in attracting micro-particles during manufacture.

Still yet another object of the present invention is to provide an acupuncture needle having a high magnetic handle that may be larger in size in comparison to the shaft, to provide a larger magnetic force while not increasing the likelihood of micro-practical attraction to the shaft during manufacturing.

Another object of the present invention is to provide an acupuncture needle having a method of joining the needle shaft to a magnetic handle by means of plastic injection and forming.

Yet another object of the present invention is to provide an acupuncture needle having a handle that may be formed and attached to the needle shaft by means of injection molding mixed magnetic and plastic material or by creating a magnetic form in the process of "sintering", then inserting and gluing or otherwise attaching the shaft to the handle.

Still yet another object of the present invention is to provide an acupuncture needle having a related magnetic sleeve that a needle may be passed through one way prior to use, or placed over the needle while in use and pulled off to the side via a lateral slit. To demagnetize the needle the user may retract the sleeve in the opposite direction.

Additional objects of the present invention will appear as the description proceeds.

The present invention overcomes the shortcomings of the prior art by providing an acupuncture needle having a low magnetized or non magnetized needle shaft or shank portion and a magnetic or magnetized handle portion to deliver both penetration and magnetic treatment to an acupuncture point.

This invention overcomes low magnetic flux problems by using a highly magnetizable handle, which greatly increases the amount of flux generated over magnetization of an ordinary acupuncture needle.

Additionally the present invention provides a magnetic sleeve to optionally field magnetize or re-magnetize the shaft portion of the needle in the course of simultaneously delivering both puncturing treatment and magnetic treatment to meridians and pre-determined acupuncture points.

The foregoing and other objects and advantages will appear from the description to follow. In the description reference is made to the accompanying drawing, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawing, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

In order that the invention may be more fully understood, it will now be described, by way of example, with reference to the accompanying drawing in which.

DESCRIPTION OF THE REFERENCED NUMERALS

Figure 1:
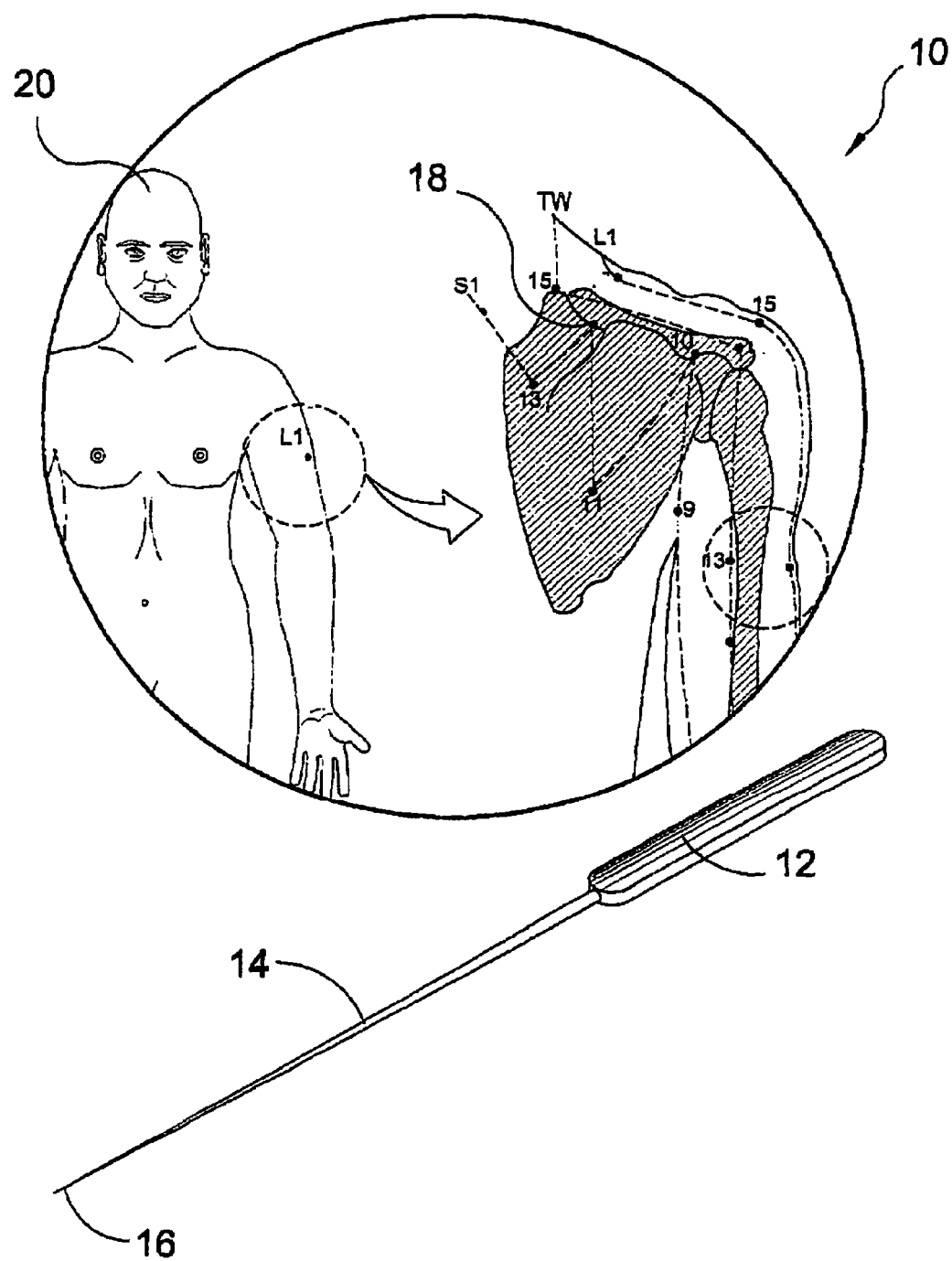
FIG. 1 is an illustrative view of the present invention in use.

Turning now descriptively to the drawings, in which similar reference characters denote similar elements throughout the several views, the figures illustrate the Acupuncture Needle with Magnetic Handle of the present invention. With regard to the reference numerals used, the following numbering is used throughout the various drawing figures.

- 10 acupuncture needle with magnetic handle of the present invention
- 12 handle portion
- 14 needle shaft
- 16 needle point
- 18 acupuncture insertion point
- 20 patient
- 22 handle insertion end of 14
- 24 receiving recess of 24
- 26 adhesive
- 28 magnetic flux
- 30 flesh of patient
- 32 magnetic sleeve
- 34 electromagnet
- 36 side slit of 32
- 38 ear needle

DETAILED DESCRIPTION OF THE PREFERRED EMBODIMENT

The following discussion describes in detail one embodiment of the invention (and several variations of that embodiment). This discussion should not be construed, however, as limiting the invention to those particular embodiments; practitioners skilled in the art will recognize numerous other embodiments as well. For definition of the complete scope of the invention, the reader is directed to appended claims.

FIG. 1 is an illustrative view of the present invention in use. The present invention relates directly to acupuncture, its practice and enhancement of the produced effects through utilization of magnetic forces. The present invention is a magnetized acupuncture needle 10 having two portions, one being a needle shaft 14 with a sharpened needle point 16 that is glued or fixed into a magnetic or magnetically chargeable handle portion 12. The needle shaft 14 is to be inserted into acupuncture insertion points 18 of a patient 20.

Figure 2:
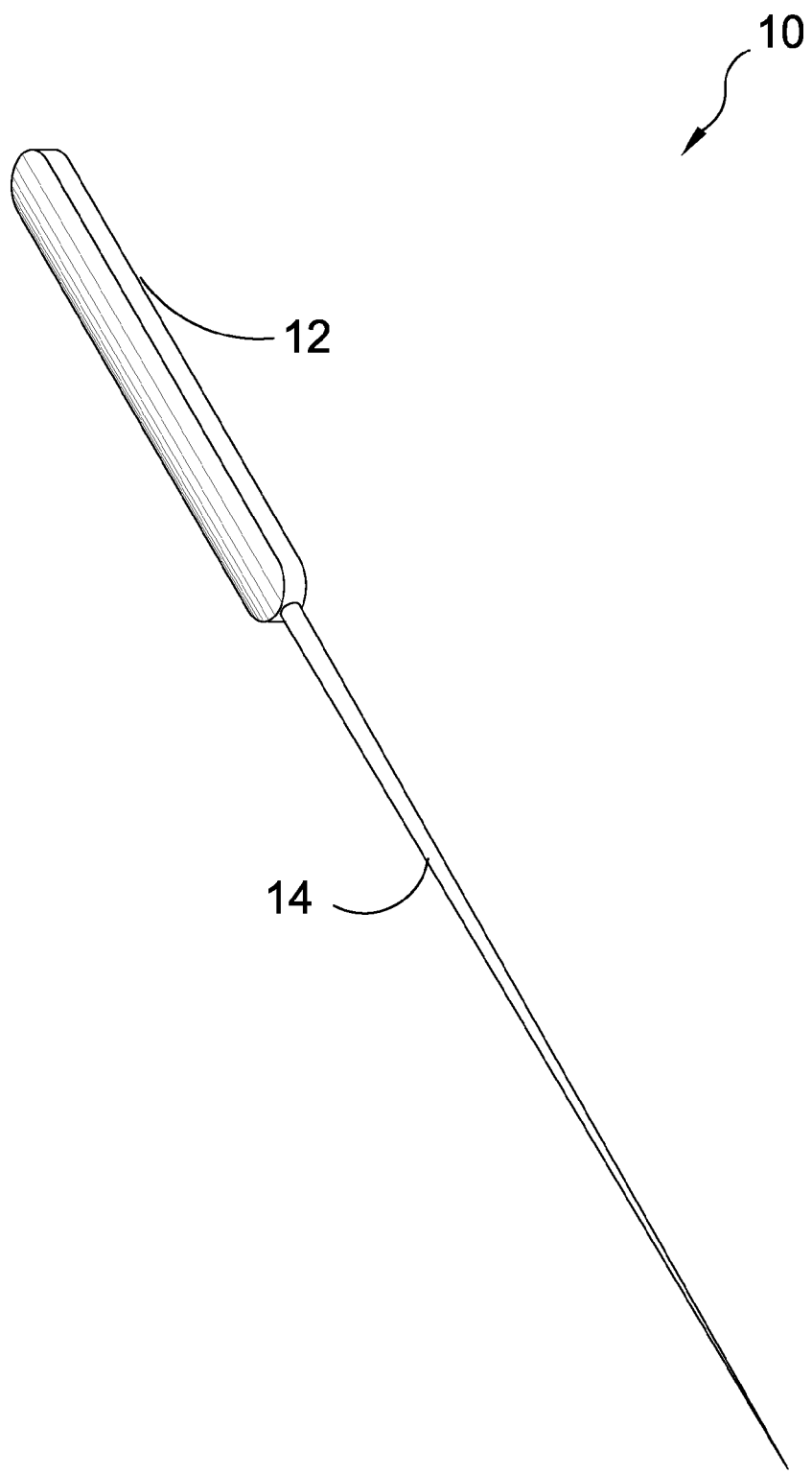
FIG. 2 is an illustrative view of the present invention.

FIG. 2 is an illustrative view of the present invention. The present invention relates directly to acupuncture, its practice and enhancement of the produced effects through utilization of magnetic forces. Depicted is the acupuncture needle of the present invention comprising two portions, the needle shaft 14 and a magnetic or magnetically chargeable handle portion 12.

Figure 3:
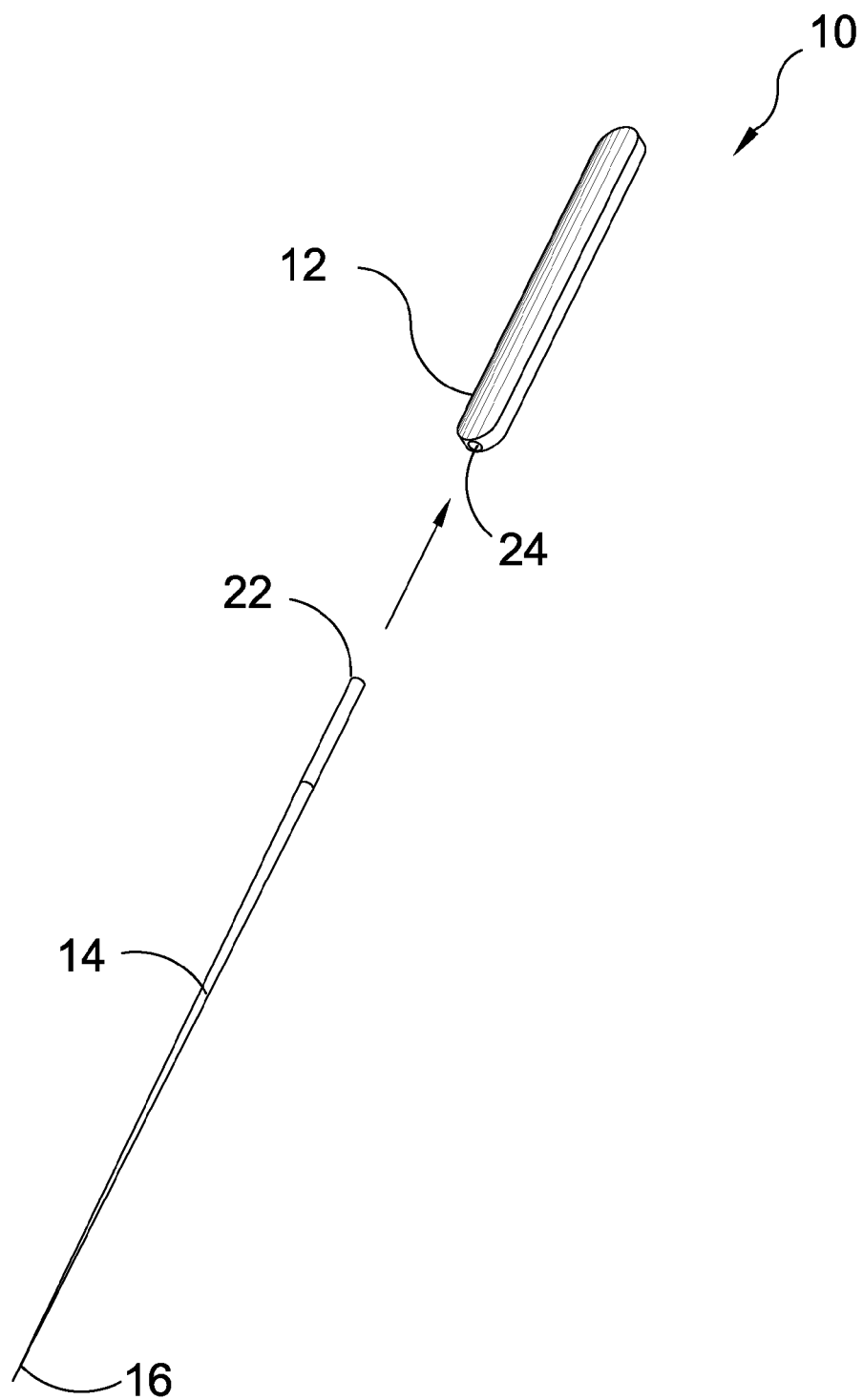
FIG. 3 is an exploded view of the acupuncture needle.

FIG. 3 is an exploded view of the acupuncture needle 10. Shown is the present invention comprising two portions, the needle shaft 14 having a first end with a needle point 16 and a second insertion end 22 and a magnetic handle portion 12 that has a receiving recess 24 for receiving the insertion end 22 of the shaft 14 and once inserted therein are bonded together forming a needle wherein the magnetized handle portion 12 may transmit an electromagnetic flux down the shaft 14 and into the acupuncture point.

Figure 4:
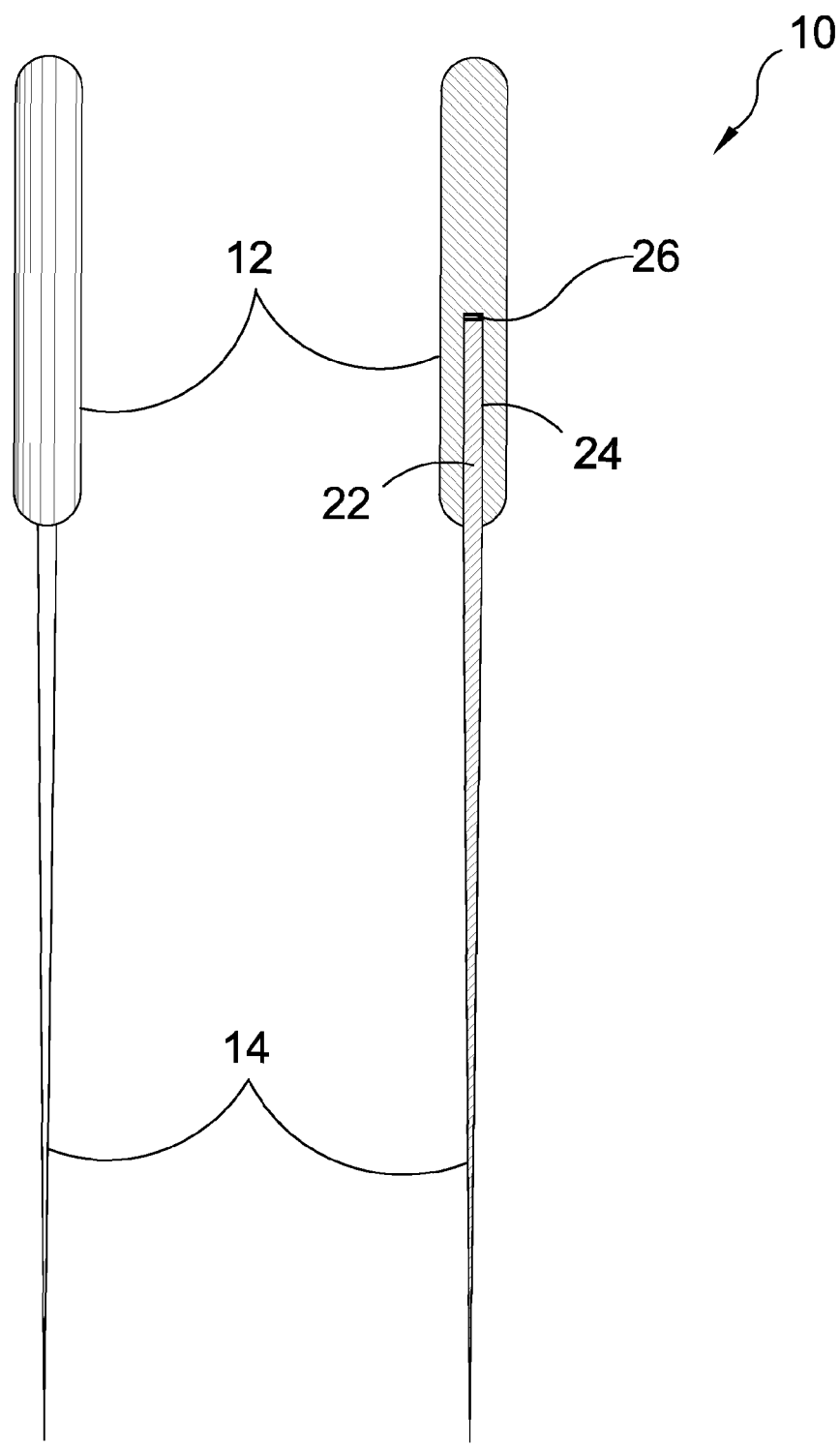
FIG. 4 is a side sectional view of the present invention.

FIG. 4 is a side sectional view of the present invention. Shown is the present invention being composed of two portions, first said portion being a sharp needle shaft 14, while the second portion being a magnetic handle portion 12 presenting a receiving recess 24 at one end whereby the insertion end 22 of the shaft 14 may be inserted and bound into the handle by an adhesive 26 or physical means such as injection molding onto the needle shaft.

Figure 5:
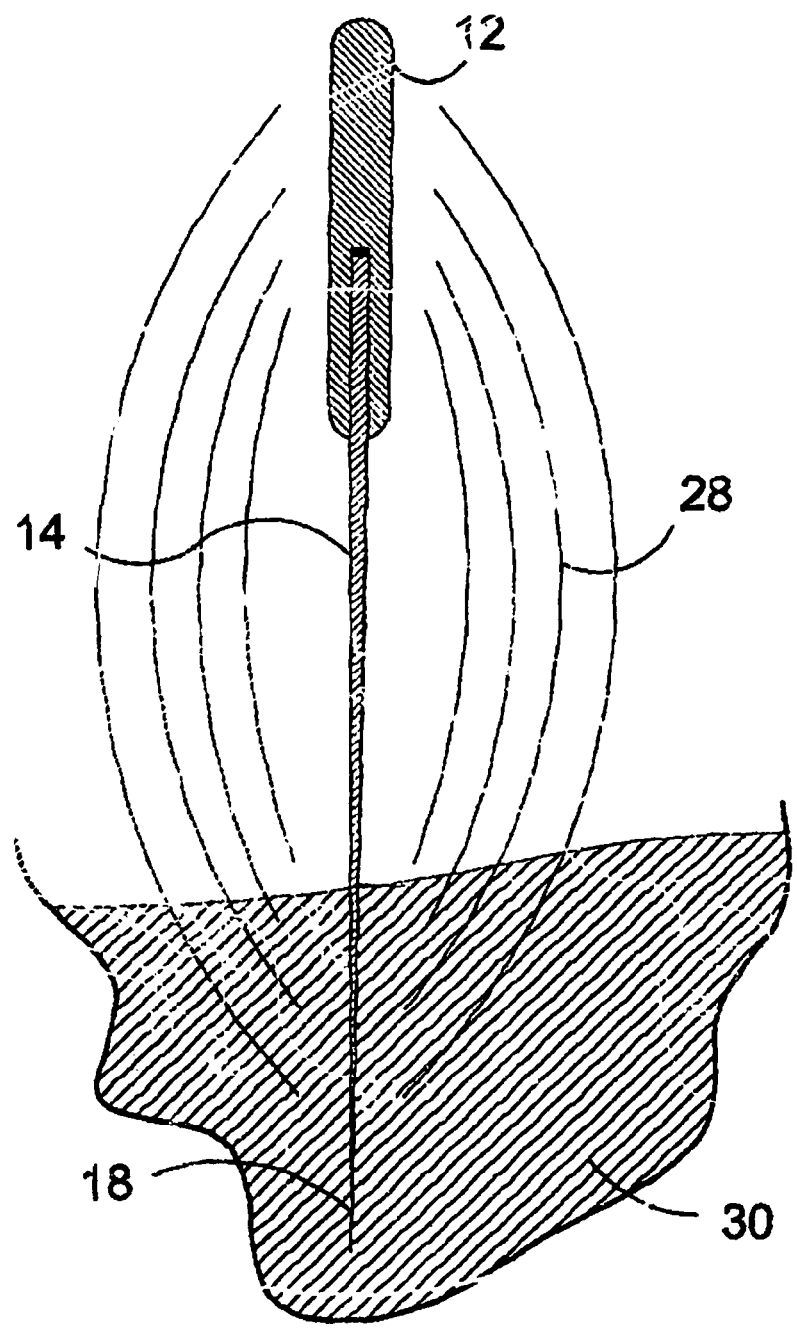
FIG. 5 is a side sectional view of the magnetic needle in use.

FIG. 5 is a side sectional view of the magnetic needle 10 in use. The present invention is an acupuncture needle comprised of a shaft 14 and a highly magnetized or magnetizable handle portion 12 that produces a magnetic flux 28 to the insertion point 18 of the patient's flesh 30.

Figure 6:
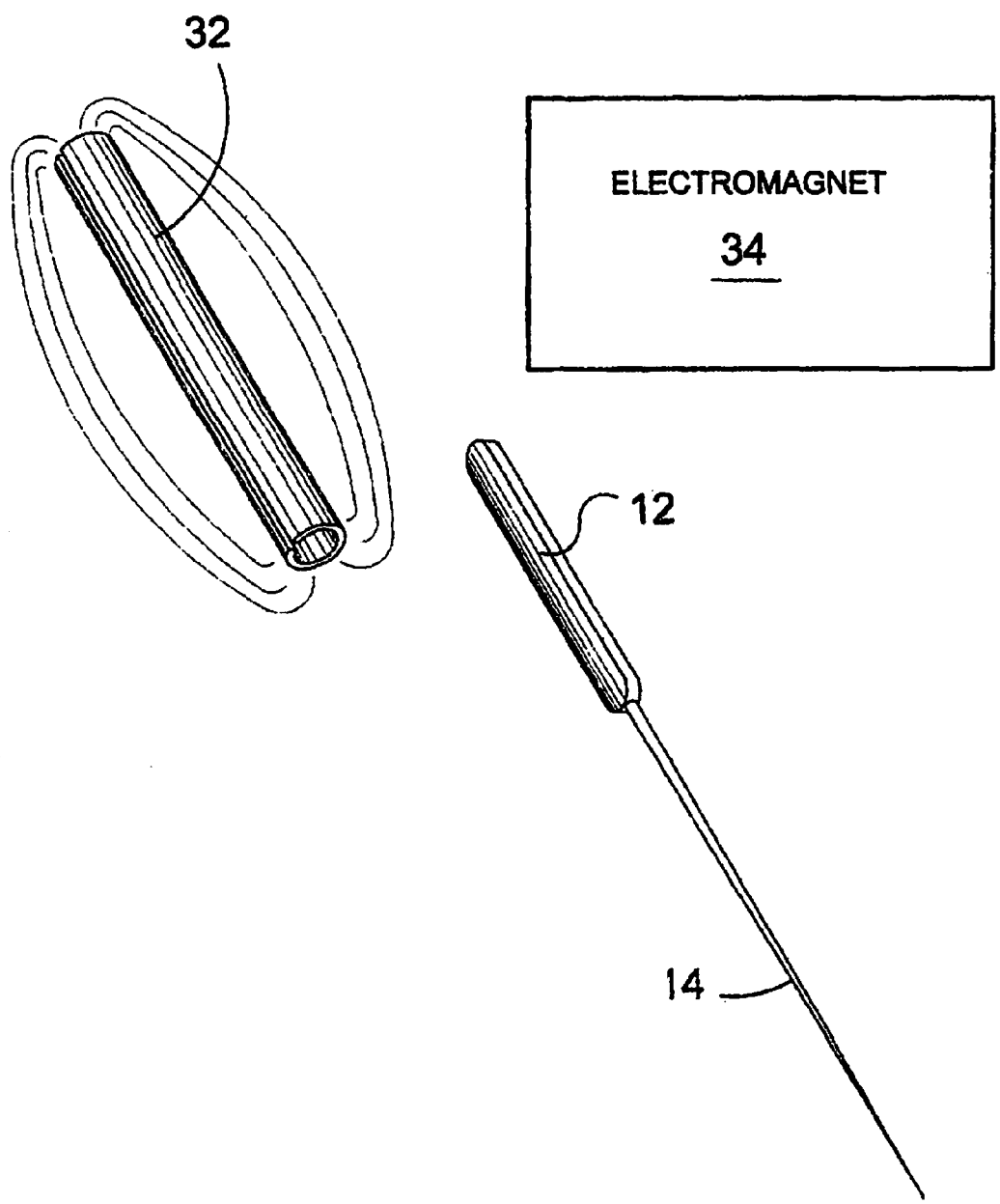
FIG. 6 is a perspective view of an additional element of the present invention.

FIG. 6 is a perspective view of an additional element of the present invention. Shown is the present invention comprising a needle shaft 14 and a handle portion 12, handle being of highly magnetizable material. The present invention provides that the needle shaft 14, particularly the highly magnetic handle portion 12 can have a magnetic field imposed upon it prior to or during an acupuncture treatment through use of a magnetic sleeve 32 or other electro magnetic 34 treatment.

Figure 7:
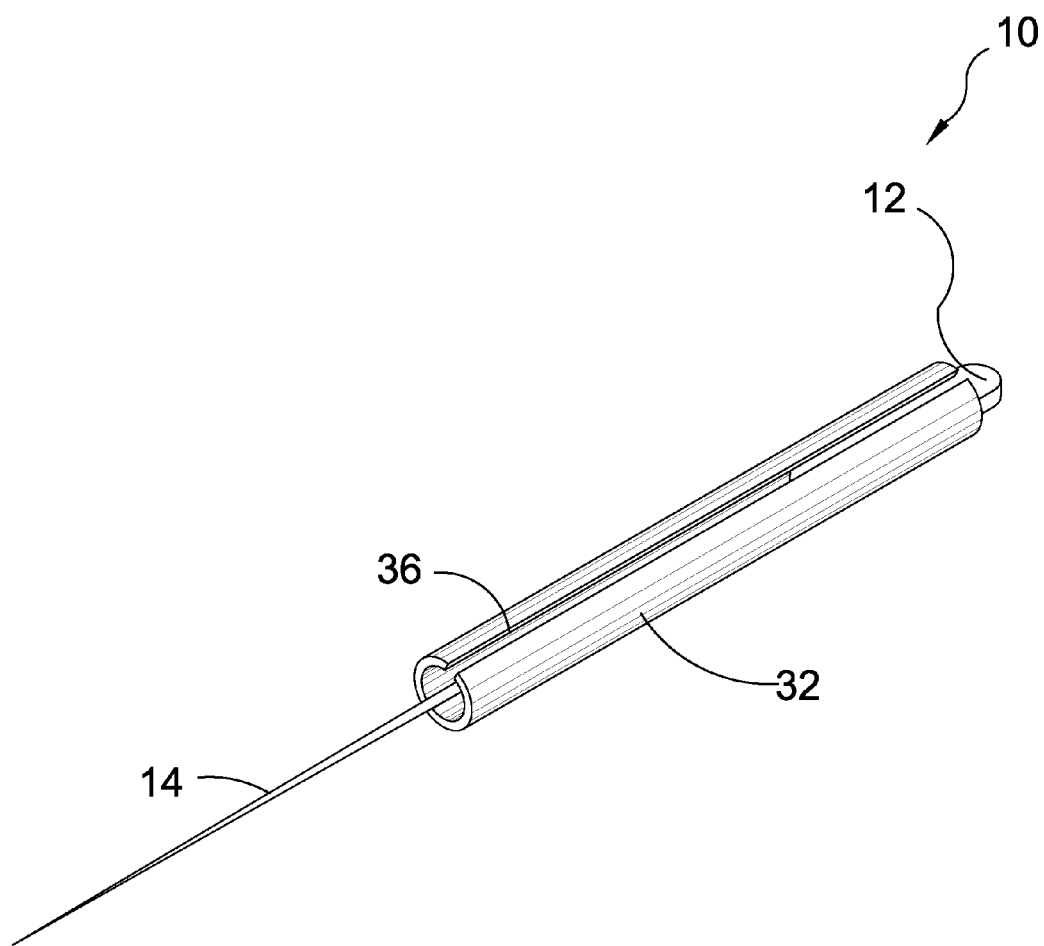
FIG. 7 is a perspective view of the magnetic sleeve being used on the needle of the present invention.

FIG. 7 is a perspective view of the magnetic sleeve 32 being used on the needle of the present invention. The magnetic sleeve 32 can be placed over the handle portion 12 to induce a magnetic flux that is then applied to the shaft 14. The magnetic sleeve 32 may be removed during use through a side slit 36.

Figure 8:
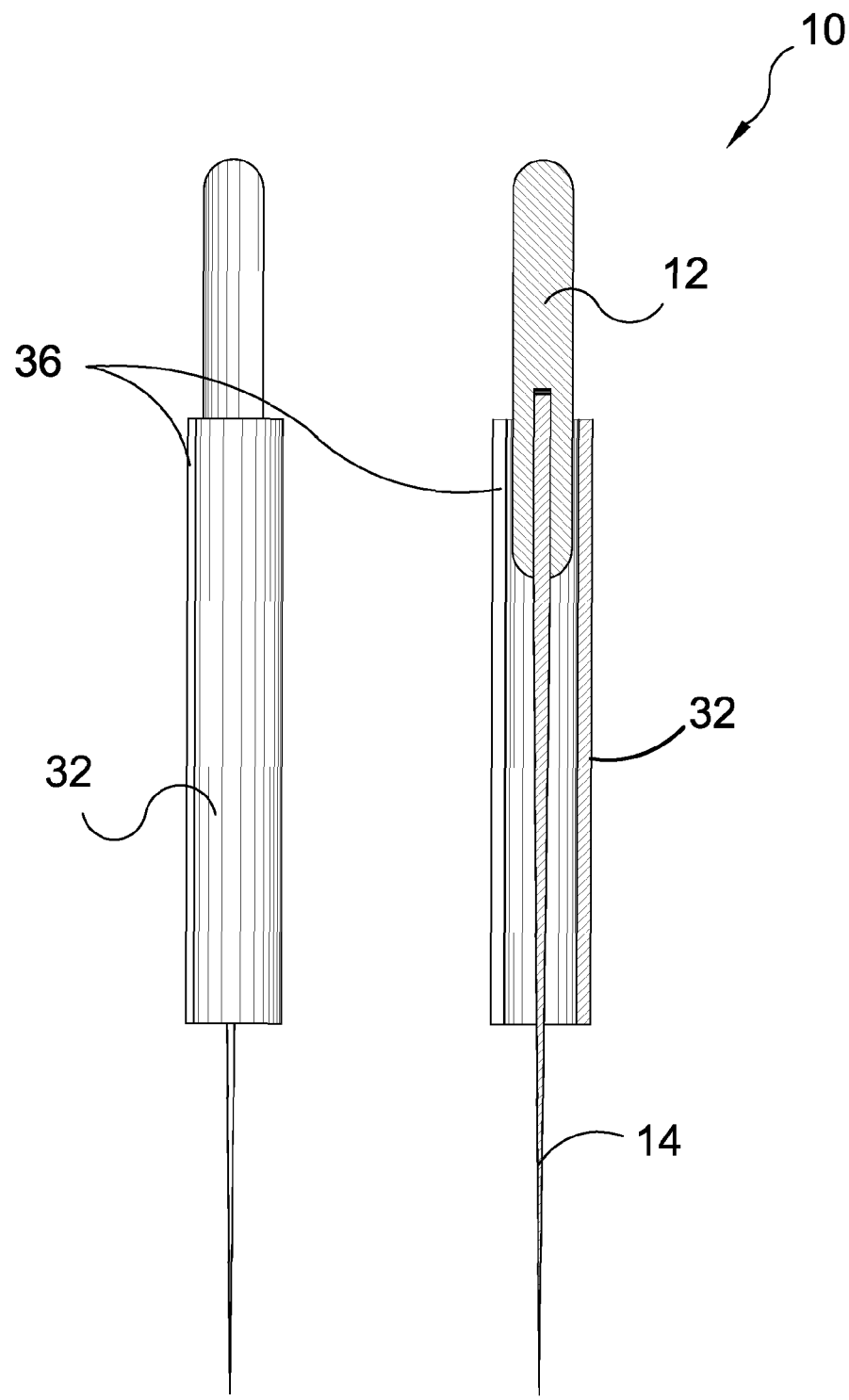
FIG. 8 is a side sectional view of the magnetic sleeve being used on the present invention.

FIG. 8 is a side sectional view of the magnetic sleeve 32 being used on the present invention. Shown is a side sectional view of the present invention depicting a highly magnetizable handle portion, 12 and a shaft 14. The handle portion 12 may be magnetized in manufacture or may be magnetized in the field by use of a magnetic sleeve 32. In the present invention the sleeve 32 has a slit 36 down its side for removal of the sleeve from the needle in a parallel manner.

Figure 9:
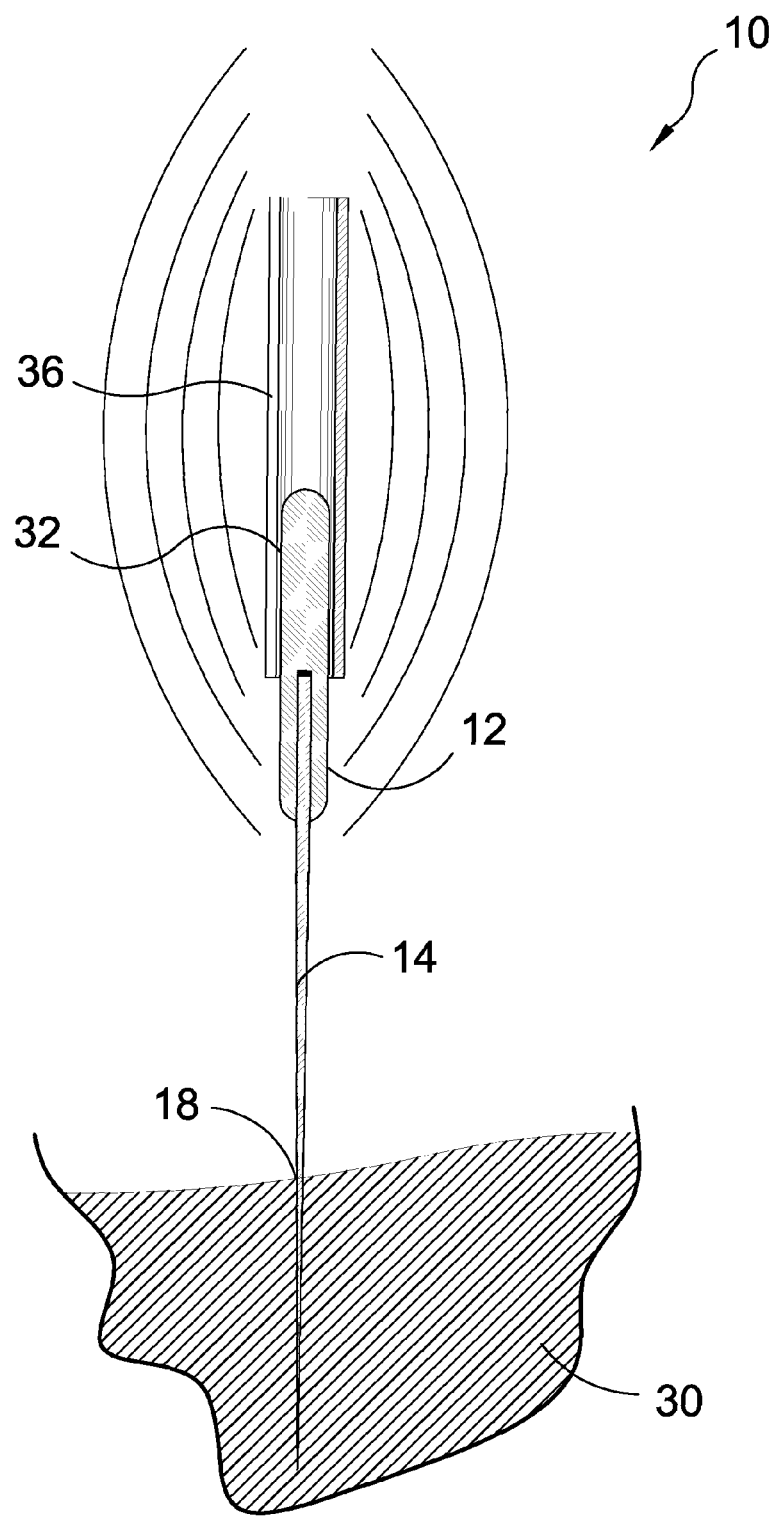
FIG. 9 is a side sectional view of the magnetic sleeve being used on the present invention while in use.

FIG. 9 is a side sectional view of the magnetic sleeve 32 being used on the present invention while in use. The magnetizing sleeve 32 may be used prior to insertion of the needle shaft 14 or may be applied over the handle portion 12 after insertion into the acupuncture point 18 of the patient's flesh 30 in which case a slit 36 is provided in the sleeve 32 to allow removal from the needle from the side so that the magnetic charge will remain after removal of the shaft.

Figure 10:
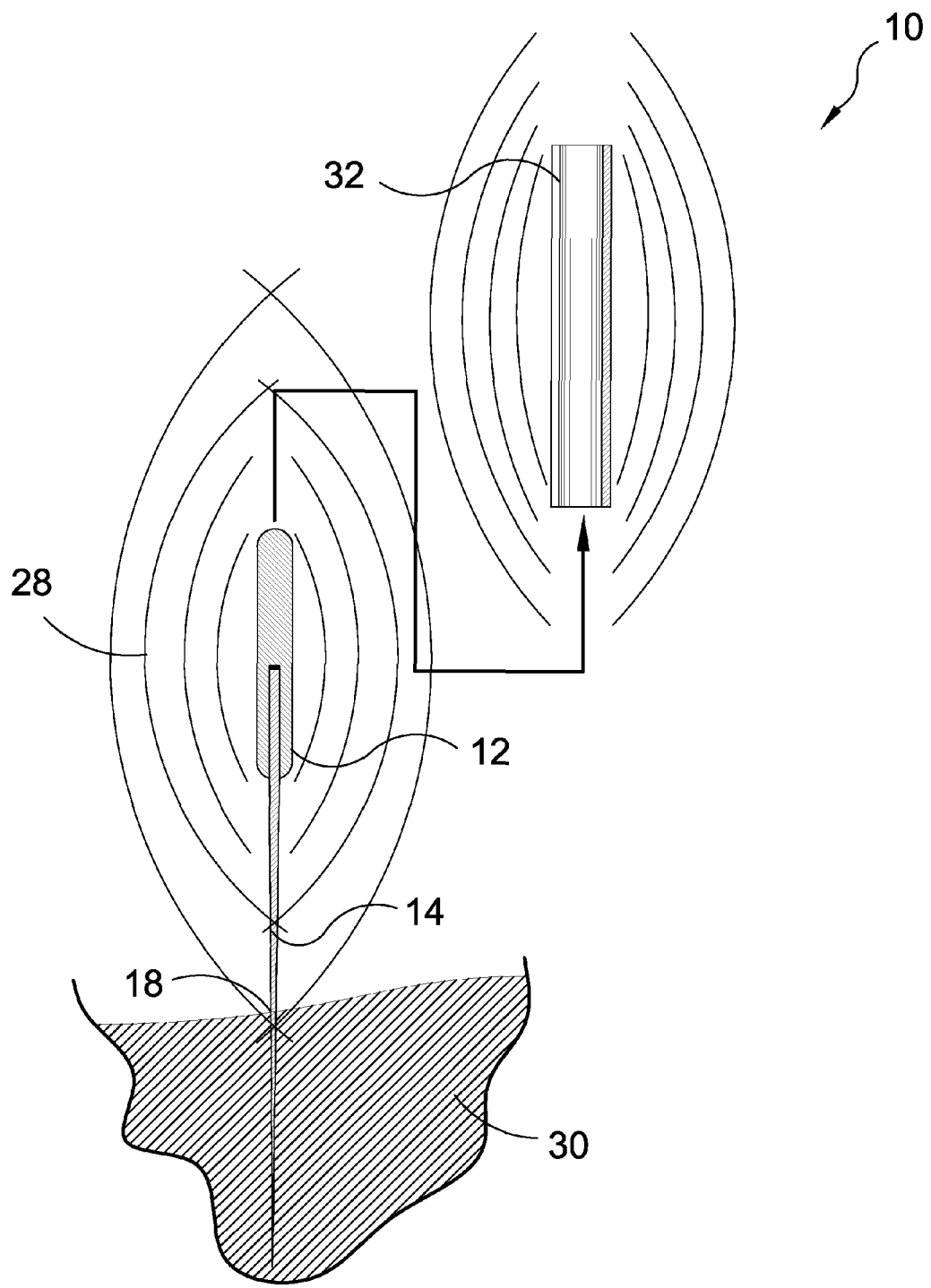
FIG. 10 is a side sectional view of the magnetic sleeve being used on the present invention while in use.

FIG. 10 is a side sectional view of the magnetic sleeve 32 being used on the present invention while in use. Shown is the present invention introduced to a patient's acupuncture point 18 whereby the magnetic handle portion 12 of the present invention has been magnetized to the extent whereby lines of magnetic flux 28 extend into a patient's flesh 30 to magnetically enhance the effects of the acupuncture needle shaft 14.

Figure 11:
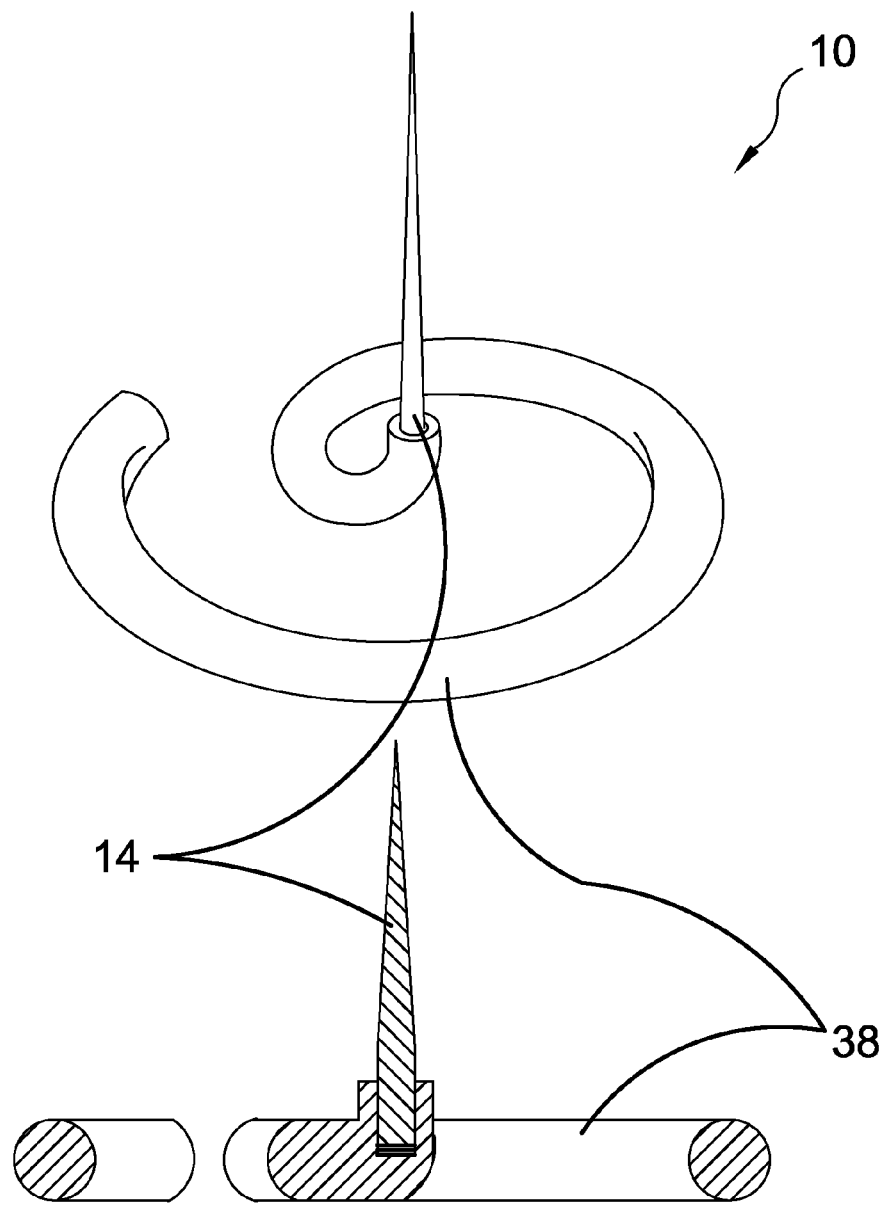
FIG. 11 is a side sectional view of the present invention in the form of an ear needle.

FIG. 11 is a side sectional view of the present invention in the form of an ear needle 38. Shown is the present invention in the form of an ear needle 38 whereby the magnetized portion forms the handle or coiled (or other shaped) shaft being joined to the needle shaft 14 portion.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is:

1. An acupuncture system capable of applying both penetration and magnetic flux to an acupuncture point comprising:
    an acupuncture needle comprising:
        a highly magnetizable handle portion; and
        a needle shaft portion projecting from said handle portion for transferring any magnetic flux from said handle portion to the acupuncture point; and
    a magnetic sleeve capable of surrounding and sliding axially along said acupuncture needle for applying a magnetic charge to said handle portion when said sleeve is placed onto said handle and needle portions while said acupuncture needle is penetrating the acupuncture point,
    wherein said sleeve comprises a slot extending a full length thereof for allowing said sleeve to be removed laterally from said acupuncture needle to avoid demagnetizing said handle portion when said sleeve is removed from said acupuncture needle.

2. The acupuncture system capable of applying both penetration and magnetic flux to an acupuncture point according to claim 1, wherein said needle portion is nonmagnetic.

3. The acupuncture system capable of applying both penetration and magnetic flux to an acupuncture point according to claim 1, wherein said needle portion has a first pointed end and a second handle insertion end.

4. The acupuncture system capable of applying both penetration and magnetic flux to an acupuncture point according to claim 3, wherein said handle portion further includes a receiving recess for the insertion of said handle insertion end of said needle portion and an adhesive for securing said needle portion to said handle portion.

5. The acupuncture system capable of applying both penetration and magnetic flux to an acupuncture point according to claim 1, wherein said magnetic charge is produced by neodymium iron boron associated with said handle portion.

6. The acupuncture system capable of applying both penetration and magnetic flux to an acupuncture point according to claim 5, wherein said neodymium iron boron is mixed with a polymeric substance.

7. The acupuncture system capable of applying both penetration and magnetic flux to an acupuncture point according to claim 5, wherein said neodymium iron boron is glued to said handle portion.

8. The acupuncture system capable of applying both penetration and magnetic flux to an acupuncture point according to claim 1, wherein said handle portion is co-linear with said needle portion.

9. The acupuncture system capable of applying both penetration and magnetic flux to an acupuncture point according to claim 1, wherein said handle portion is helical and adapted to be mounted on an ear of a subject.

10. A method of applying both penetration and magnetic flux to an acupuncture point comprising the steps of:
    penetrating an acupuncture point of a subject with an acupuncture needle comprising a magnetizable handle portion and a needle portion projecting from said handle portion;
    sliding axially a magnetic sleeve over and surrounding said acupuncture needle while said acupuncture needle is penetrating the acupuncture point to apply a magnetic charge to said handle portion of said acupuncture needle, thereby transferring magnetic flux to the acupuncture point; and
    removing said sleeve from said acupuncture needle without demagnetizing said acupuncture needle.

11. The method of applying both penetration and magnetic flux to an acupuncture point according to claim 10, wherein said sleeve comprises a slot extending a full length thereof for allowing said sleeve to be removed laterally from said acupuncture needle to avoid demagnetizing said handle portion when said sleeve is removed.

* * * * *